(12) United States Patent
Murphy

(10) Patent No.: US 9,289,235 B2
(45) Date of Patent: Mar. 22, 2016

(54) BONE AUGMENTATION APPARATUS

(76) Inventor: Kieran P. Murphy, Baltimore, MD (US)

( * ) Notice: Subject to any disclaimer, the term of this patent is extended or adjusted under 35 U.S.C. 154(b) by 915 days.

(21) Appl. No.: 12/063,618

(22) PCT Filed: Aug. 17, 2006

(86) PCT No.: PCT/US2006/032242
§ 371 (c)(1),
(2), (4) Date: Feb. 21, 2008

(87) PCT Pub. No.: WO2007/024641
PCT Pub. Date: Mar. 1, 2007

(65) Prior Publication Data
US 2008/0195114 A1 Aug. 14, 2008

Related U.S. Application Data

(60) Provisional application No. 60/709,824, filed on Aug. 22, 2005.

(51) Int. Cl.
| | | |
|---|---|---|
| *A61B 17/58* | (2006.01) | |
| *A61B 17/60* | (2006.01) | |
| *A61F 2/00* | (2006.01) | |
| *A61B 17/34* | (2006.01) | |
| *A61B 17/88* | (2006.01) | |
| *A61F 2/44* | (2006.01) | |
| *A61F 2/46* | (2006.01) | |

(52) U.S. Cl.
CPC ......... *A61B 17/3472* (2013.01); *A61B 17/8811* (2013.01); *A61B 17/8816* (2013.01); *A61B 17/8822* (2013.01); *A61F 2/44* (2013.01); *A61F 2/4611* (2013.01); *A61F 2002/4623* (2013.01); *A61F 2002/4677* (2013.01)

(58) Field of Classification Search
CPC .................. A61B 17/3472; A61B 17/8816
USPC ..................................................... 606/92–94
See application file for complete search history.

(56) References Cited

U.S. PATENT DOCUMENTS

| | | | |
|---|---|---|---|
| 4,815,454 A | 3/1989 | Dozier, Jr. | |
| 4,930,525 A | 6/1990 | Palestrant | 128/898 |
| 4,993,948 A | 2/1991 | Cameron et al. | |
| 5,263,748 A * | 11/1993 | Carstensen | 285/333 |

(Continued)

FOREIGN PATENT DOCUMENTS

| | | |
|---|---|---|
| EP | 1 074 231 A1 | 2/2001 |
| JP | 1-74944 U | 5/1989 |

(Continued)

OTHER PUBLICATIONS

International Search Report dated Feb. 12, 2007.

*Primary Examiner* — David Bates
*Assistant Examiner* — Olivia C Chang
(74) *Attorney, Agent, or Firm* — Perry + Currier Inc.

(57) ABSTRACT

A bone cement apparatus (20) is provided. In an embodiment, the apparatus includes a syringe (24) and a needle (120). The syringe and needle are interconnected by a connecting tube (32). Various fittings are employed to join the syringe, needle and connecting tube. The connecting tube and fittings present a pathway along which bone cement is carried. The connecting tube, fittings, and needle are all configured such that a substantially uniform pathway is provided from the end of the syringe to the end of the needle.

15 Claims, 7 Drawing Sheets

(56) References Cited

U.S. PATENT DOCUMENTS

| | | | |
|---|---|---|---|
| 5,375,588 A | 12/1994 | Yoon | 128/4 |
| 6,033,411 A | 3/2000 | Preissman | 606/99 |
| 6,348,055 B1 | 2/2002 | Preissman | 606/94 |
| 6,488,667 B1 | 12/2002 | Murphy | 604/272 |
| 6,676,664 B1* | 1/2004 | Al-Assir | 606/94 |
| 6,679,886 B2* | 1/2004 | Weikel et al. | 606/79 |
| 2002/0001470 A1 | 1/2002 | Linnecke | |
| 2002/0013553 A1* | 1/2002 | Pajunk et al. | 604/187 |
| 2002/0156376 A1 | 10/2002 | Wang et al. | 600/439 |
| 2003/0014056 A1 | 1/2003 | Tague et al. | 606/94 |
| 2004/0024410 A1* | 2/2004 | Olson et al. | 606/93 |
| 2004/0092946 A1* | 5/2004 | Bagga et al. | 606/93 |
| 2004/0153053 A1 | 8/2004 | Ishikawa | |
| 2005/0070915 A1* | 3/2005 | Mazzuca et al. | 606/93 |
| 2007/0233149 A1 | 10/2007 | Bohner et al. | |

FOREIGN PATENT DOCUMENTS

| | | |
|---|---|---|
| JP | 2004501716 A | 1/2004 |
| WO | WO 02/02033 A | 1/2002 |
| WO | 2005/074840 | 8/2005 |

* cited by examiner

BONE AUGMENTATION APPARATUS

CROSS REFERENCE TO RELATED APPLICATIONS

The present application is a 35 U.S.C. §371 National Phase conversion of PCT/US2006/032242 filed Aug 17, 2006, which claims priority of U.S. Provisional Application No. 60/709,824.

FIELD OF THE INVENTION

The present invention relates generally to bone augmentation and in particular an apparatus for performing bone augmentation.

BACKGROUND OF THE INVENTION

Vertebroplasty is a well-known procedure for augmenting a vertebrae that has collapsed due to osteoporosis or other indication. See, for example, U.S. Pat. No. 6,273,916 to Murphy ("Murphy #1") and issued Aug. 14, 2001, the contents of which are incorporated herein by reference. In general terms, vertebroplasty involves transpedicular or posterolateral injection of a bone cement into the vertebral body.

As is described in Murphy #1 and elsewhere, various types of bone cements can be used. One common bone cement is polymethylmethacrylate, but other types will occur to those of skill in the art. A common feature of many bone cements, is that they have a viscosity such that substantial pressure can be required to effect expression of the bone cement from the syringe, through any connective tubing and the needle and into the vertebral cavity. However, also as described in Murphy #1, considerable care is required to reduce the likelihood of overfilling the vertebral body, as such overfilling can rupture the spinal cord and paralyze the patient. Prior art syringes, connecting tubes and needles, however, can in some circumstances impede controlled and careful injection of bone cement into the vertebral body due to irregularities found along the channel between the syringe body and the needle tip. Such irregularities can be found, in particular examples of prior art, at luer-lock junctions for removable connections between the syringe, the connecting tube and the needle. Further viscosities of non-polymethylmethacrylate cements are generally greater than the viscosity of polymethylmethacrylate's, and such viscosities can present problems at luer-lock junctions.

Additionally, because vertebroplasty is performed under image-guidance, extra care may be taken to reduce the radiologist's (or other medical professional performing the procedure) exposure to the imaging beam under which the procedure is performed. Thus, U.S. Pat. No. 6,488,667 to Murphy ("Murphy #2") teaches a needle holder that can be used to allow the radiologist to grasp and control the needle during insertion into the vertebral body, while also allowing the radiologist to keep his or her hands farther away from the imaging beam than if the radiologist had to grasp the needle directly. While effective, one problem, however, with the needle holder in Murphy #2 is that in certain circumstances, the needle holder can slide along the length of the needle, which can interfere with the desired level of control over the needle.

SUMMARY OF THE INVENTION

It is therefore an object of the present invention to provide a novel bone augmentation apparatus that obviates or mitigates at least one of the disadvantages of the prior art.

In a first aspect of the invention there is provided a bone cement apparatus comprising a delivery reservoir for holding a bone cement and a needle for injecting the bone cement into a bone. The apparatus also comprises a passageway interconnecting the reservoir and the needle, the passageway having substantially uniform dimensions. The reservoir can be a syringe. The passageway can include a connecting tube. The passageway can include a connector for attaching the connecting tube to the delivery reservoir. The bone cement can be polymethylmethacrylate.

BRIEF DESCRIPTION OF THE DRAWINGS

Embodiments of the invention will now be discussed, by way of example only, with reference to the attached Figures, in which.

DETAILED DESCRIPTION OF THE INVENTION

Figure 1:
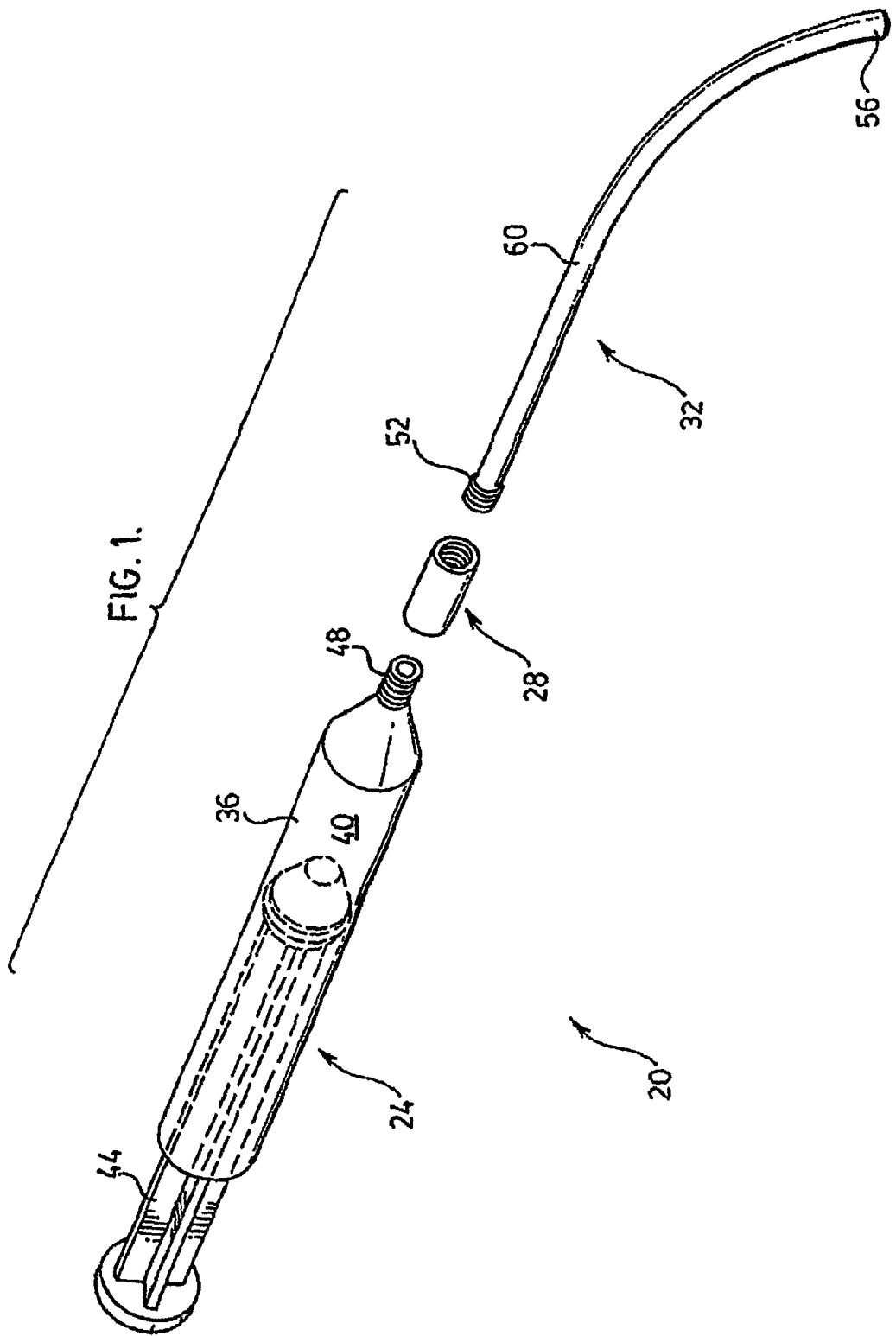
FIG. 1 shows a bone cement delivery apparatus in accordance with an embodiment of the invention.

Referring now to FIG. 1, a bone cement delivery apparatus in accordance with an embodiment of the invention is indicated generally at 20. Apparatus 20 comprises a syringe 24, a connector 28 and a connecting tube 32. Apparatus 20 is used to deliver bone cement as part of a bone augmentation procedure, and in a present embodiment the procedure is vertebroplasty.

Syringe 24 comprises a barrel 36 defining a chamber 40 through which a plunger 44 can pass in order to express a bone cement (not shown) from a distal tip 48 of syringe 24.

Connector 28 provides a fitting which can be used to releasably couple syringe 24 to tube 32, such that a channel between tip 48 and tube 32 is substantially uniform with a channel defined by tube 32. Connector 28 will be discussed in greater detail below.

Tube 32 is made any suitable flexible material and has a length of from about 10 or about 15 centimeters ("cm") to about 20 or about 30 cm; Tube 32 includes a proximal tip 52 that is releasably attachable to connector 28, and a distal tip 56 that is releasably attachable to a vertebroplasty needle (not shown). Tips 52 and 56 are joined by a body 60 that defines a passage for communicating bone cement from syringe 24 and into a vertebroplasty needle.

Syringe 24, connector 28 and tube 32 are made from known materials and have a general size and configuration that is suitable for deployment in a vertebroplasty procedure, subject to various specific features discussed herein. One example of a generally known off-the-shelf configuration is the Cook Duro-ject Bone Cement Injector, available from COOK GROUP INCORPORATED, P.O. Box 489, Bloomington, Ind. 47402-0489, USA.

Figure 2:
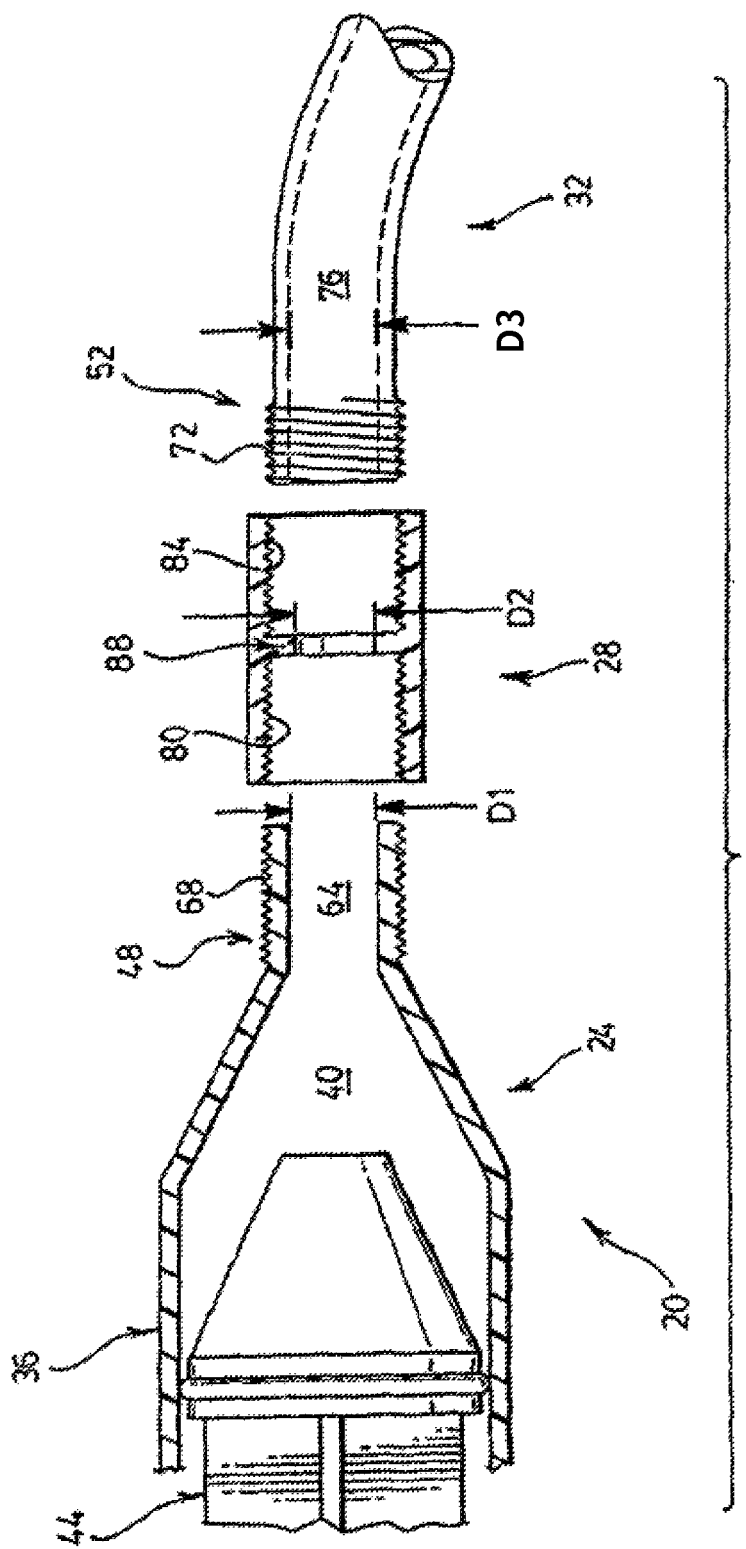
FIG. 2 shows an exploded view of a portion of the apparatus of FIG. 1.

Referring now to FIG. 2, a partial-sectional view of apparatus 20 shows distal tip 48 of syringe 24, connector 28, and proximal tip 52 of tube 32 in greater detail.

As best seen in FIG. 2, tip 48 defines a substantially uniform hollow cylindrical channel 64 having an interior diameter, the interior diameter being represented in FIG. 2 by the reference "D1". D1 is chosen according to the type of bone cement being expressed from chamber 40. Where chamber 40 has a volume of about 10 cubic centimetres ("cc"), and where the bone cement is polymethlymethacrylate, then D1 can be from about five millimeters ("mm") to about fifteen mm; or D1 can be from about seven mm to about twelve mm; or D1 can be from about eight mm to about ten mm. However, other sizes of chamber 40, dimensions of D1 and/or choices for bone cement to be expressed from chamber 40 will now occur to those of skill in the art.

Tip 48 also includes a set of exterior threads 68 along the peripheral, external surface of tip 48.

Tip 52 of tube 32 also includes a set of exterior threads 72 along the peripheral, external surface of tip 52. Tube 32 provides a passage 76 for carrying bone cement from syringe 24 to the vertebroplasty needle. Passage 76 is substantially cylindrical and has a configuration and dimensions that are substantially the same as channel 64. Thus, passage 76 has interior diameter, the interior diameter being represented in FIG. 2 by the reference "D2". Diameter D2 is substantially the same as diameter D1.

Connector 28 is substantially cylindrical and has an external surface with a substantially uniform surface. Connector 28 is characterized by a first set of interior threads 80 that are complementary to exterior threads 68, such that tip 48 can be securely fastened within connector 28 by threading threads 68 and 80 together. Likewise, connector 28 is also characterized by a second set of interior threads 84 that are complementary to exterior threads 72, such that tip 52 can be securely fastened within connector 28 by threading threads 72 and 84 together. Connector is also characterized by an interior annular flange 88. Flange 88 thus presents a substantially cylindrical opening and has a configuration and dimensions that are substantially the same as channel 64 and passage 76. Thus, passage 76 has interior diameter, the interior diameter being represented in FIG. 2 by the reference "D3". Diameter D3 is substantially the same as diameters D1 and D2.

While not required, the direction of each threads 68 and 80, and threads 72 and 84, are chosen such that, when threads 68 and 80 are engaged, and threads 72 and 84 are engaged, rotation of syringe 24 (or tube 32) in a first direction will tighten all connections between syringe 24, connector 28 and tube 32; while rotation in an opposite direction will loosen the connection between syringe 24, connector 28 and tube 32. For greater clarity, "tighten" means that tips 48 and 52 are urged towards flange 88, while "loosen" means that tips 48 and 52 are urged away from flange 88.

While not shown in figures, those of skill in the art will now appreciate that when tip 48 is fully tightened within connector 28 such that tip 48 abuts flange 88; and when tip 52 is fully tightened within connector 28 such that tip 52 abuts the opposite side of flange 88, then a substantially uniform passage is provided between chamber 40 and the vertebroplasty needle (not shown) connected to tip 56.

Figure 3:
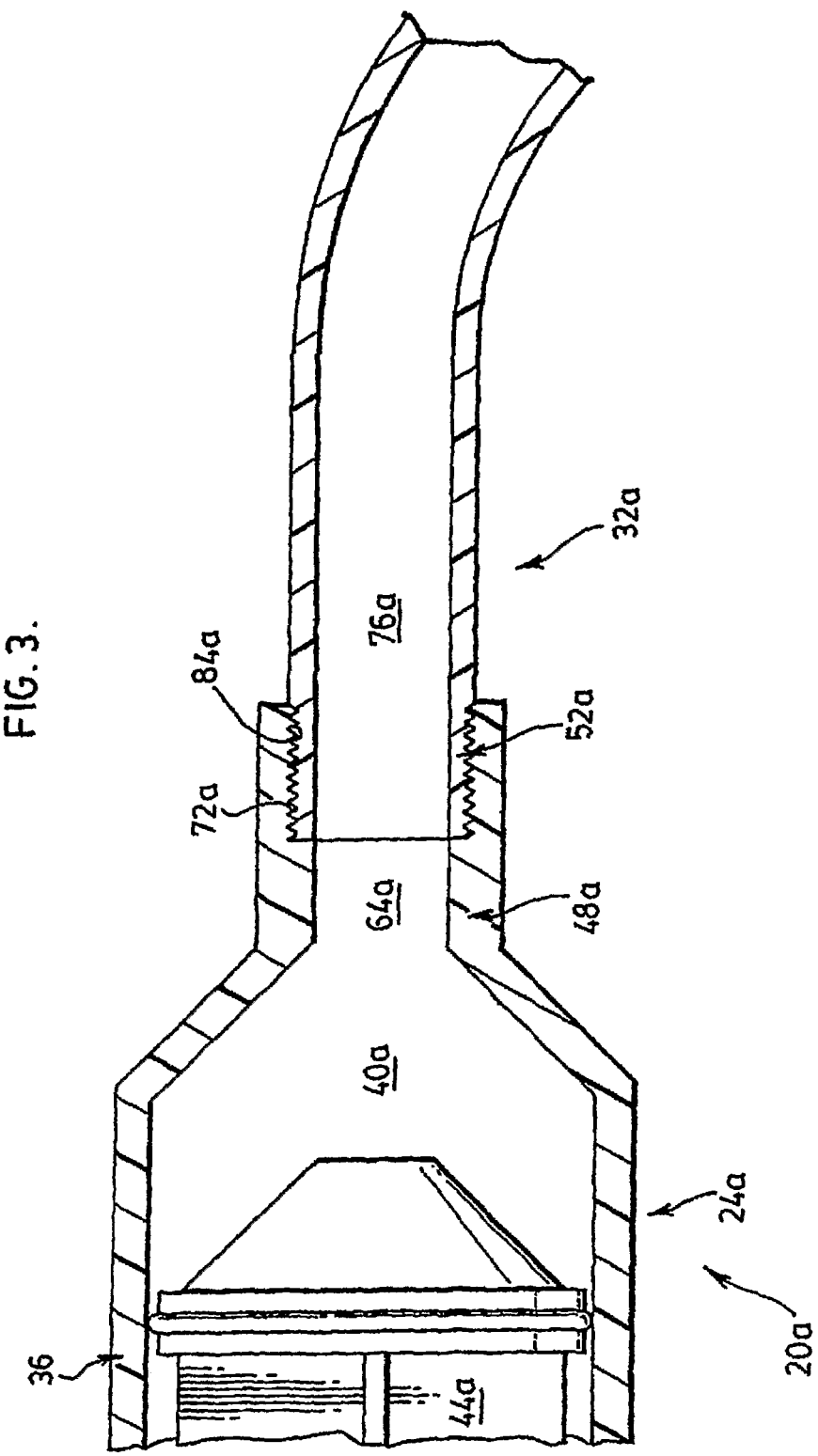
FIG. 3 shows a bone cement delivery apparatus in accordance with another embodiment of the invention.
Figure 4:
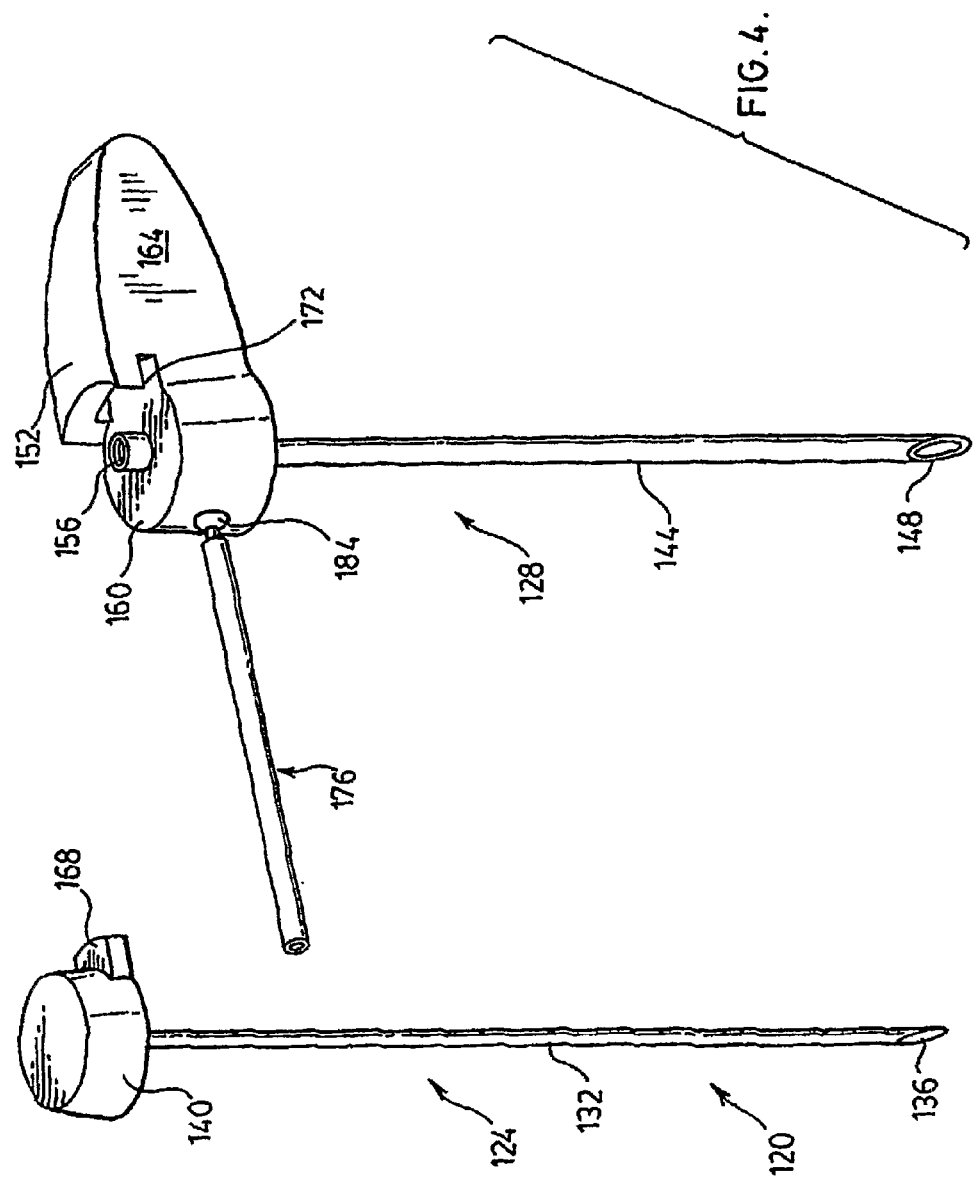
FIG. 4 shows an, exploded view of a needle in accordance with another embodiment of the invention.

Another embodiment of the invention is shown in FIG. 3, which shows a bone cement delivery apparatus 20a. Apparatus 20a shares a number of common components with apparatus 20, and like components include like references, but followed by the suffix "a". Of note, apparatus 20a does not include a connector like connector 28 from apparatus 20. Rather, the functionality of connector 28 is integral with tip 48a. Tip 48a is provided with a channel 64a having a first diameter, and a set of interior threads 84a which are formed on an interior surface of tip 48a having a second diameter greater than the first diameter. The second diameter corresponds with the outside diameter of tip 52a. Threads 84a are thus complementary to exterior threads 72a of tip 52a. It will now be apparent that while FIGS. 2 showed apparatus 20 unassembled, in FIG. 3, apparatus 20a is assembled. Thus, in FIG. 3, a substantially uniform passage can be seen between chamber 40a and passage 76a.

Once each are assembled, the operation of apparatus 20 and apparatus 20a is substantially the same. For ease of reference, only apparatus 20 will be discussed further in this description of operation, but those of skill in the art will recognize that such discussion is applicable to apparatus 20. In operation, apparatus 20 will be assembled (similar to the assembled depiction of apparatus 20a in FIG. 3) so that a substantially secure and sealed connection is made between syringe 24 and tube 32. Syringe 24 and tube 32 are thus "tightened" within connector 28, thereby providing a substantially uniform passage from chamber 40 to passage 76. Next, plunger 44 is removed from barrel 36 and chamber 40 is filled with a bone cement. Plunger 44 is then reinserted into barrel 36. As plunger 44 is depressed, bone cement is urged into channel 64, through the opening defined by flange 88 and into passage 76. Because the path defined by channel 64, the opening defined by flange 88 and passage 76 are substantially uniform, the turbulence and other disturbances to the flow of bone cement are reduced, thereby easing the effort on the part of the surgeon depressing plunger 44, and allowing that surgeon to have improved predictability as to the rate by which bone cement will be expressed from the vertebroplasty needle connected to tip 56.

Another embodiment of the invention is shown in FIGS. 4-7, which shows a needle 120 for use in a bone augmentation procedure. If desired, and while not required, apparatus 120 can be used in conjunction with apparatus 20 or apparatus 20a. Needle 120 includes a stylet 124 and a trocar 128 for receiving stylet 124. When assembled, stylet 124 and trocar 128 provide a solid instrument for piercing a vertebral body, as is described in Murphy #2.

Stylet 124 is characterized by a shaft 132 with a piercing tip 136 and a grip 140 located on the end of shaft 132 opposite tip 136. Trocar 128 is characterized by a duct 144 and an open tip 148 and a handle 152 located on the end of duct 140 opposite tip 148. The overall configuration, size, length, and other features (such as length of shaft 132 and duct 140 or shape of the complementary tips 136 or 148) of stylet 124 and trocar 128 is not particularly limited and can be chosen according to the desired vertebroplasty or other bone augmentation procedure.

Figure 5:
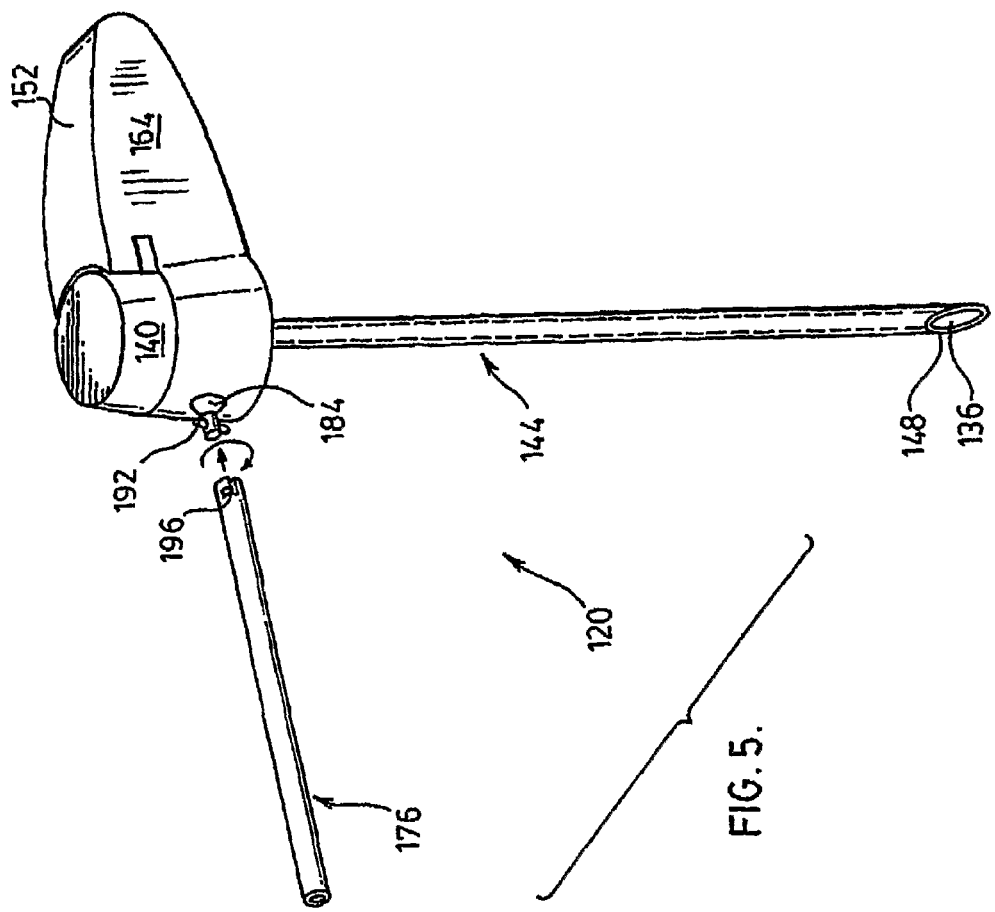
FIG. 5 shows the needle of FIG. 4 when it is assembled.

Tip 136 is receivable into an opening 156 located on handle 152. Opening 156 is located on a cut-away section 160 of handle 152. Cut-away section 160 is adjacent to a knob 164 that can be grasped. Cut-away section 160 is complementary in shape to grip 140. As best seen in FIG. 5, when stylet 124 is assembled to trocar 128, grip 140 and handle 152 present a substantially solid, and contiguous mass that presents a striking surface for a hammer. As known to those skilled in the art, such a hammer is used to drive tips 136 and 148 into the vertebrae (or other bone location for which an augmentation procedure can be desired.)

Needle 120 also includes a lock for affixing grip 140 within cut-away section 160. The lock can take a variety of desired configurations, but in a present embodiment the lock includes a tab 168 located on grip 140 and a complementary groove 172 on handle 152. Thus, once stylet 124 is inserted into groove 152, grip 140 can be rotated so as to engage tab 168 within groove 172 in a locked position. In this locked position (best seen in FIG. 5), tips 136 and 148 are aligned to present a contiguous piercing surface. In an unlocked position, stylet 124 can be removed from trocar 128.

Figure 6:
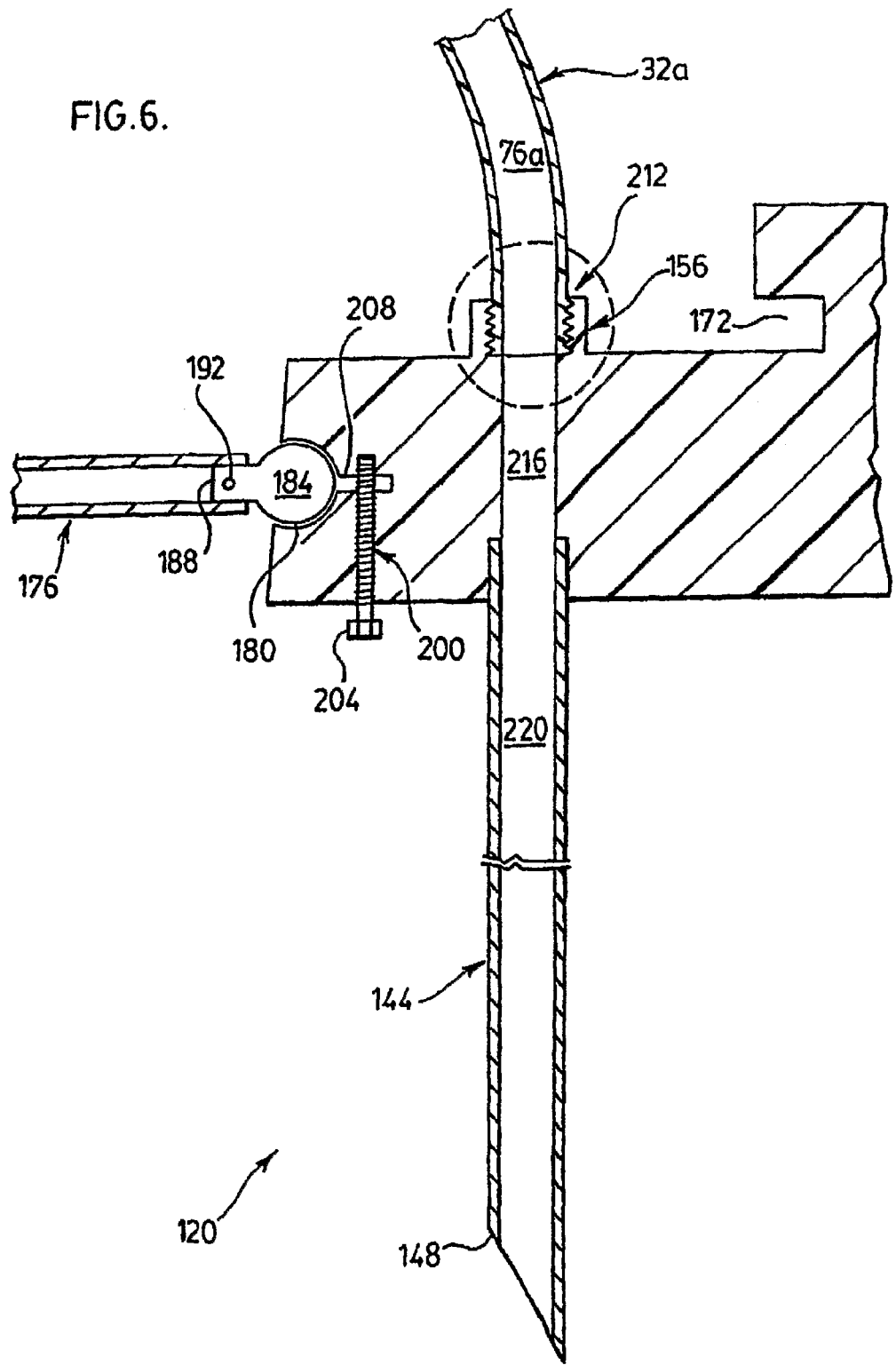
FIG. 6 shows a partial sectional view of the needle of FIGS. 4 and 5.

Needle 120 also includes a holder 176 that is removably attachable to handle 152. In a present embodiment, and as best seen in FIG. 6, handle 152 include a spherical socket 180 for receiving a ball 184. Ball 184 is substantially spherical and slightly smaller than socket 180. Ball 184 includes a protrusion 188 that itself includes a pair of arms 192. As best seen in FIGS. 5 and 6, arms 192 fit into a complementary pair of grooves 196 located on holder 176, so that that holder 176 can be removably attached to handle 152.

Handle 152 also includes a tensioning mechanism 200. In a present embodiment, tensioning mechanism includes a set screw 204 that is rotatable so as to urge a pin 208 into, or out of, engagement with ball 184. Depending on the degree to which pin 208 is engaged with ball 184, ball 184 will either freely rotate within socket 180, or be held in a substantially fixed location within ball 184. Adjusting screw 204 varies the amount of force applied to ball 184, thereby affecting the amount of force that is applied to holder 176 to move holder 176 in relation to handle 152.

Also in FIG. 6, needle 120 is shown connected to apparatus 20a. Specifically, tube 32a is shown connected to opening 156. Of note, a fitting to connect tube 32a opening 156 is indicated at 212. Fitting 212 is configured in substantially the same manner as the fitting between tip 52a and 48a shown in FIG. 3. In general terms, fitting 212 is thus structured to provide a secure fit between tube 32a and needle 120, while also providing a substantially uniform pathway for bone cement to travel. Thus, handle 152 includes a passage 216 in communication with passage 76a. Passage 216 is substantially the same configuration and dimension as passage 76a. Duct 144 also includes a passage 220 in communication with passage 216. Passage 220 is substantially the same configuration and dimension as passage 216. Thus, when bone cement is passed through passage 76a, it is carried through an overall path of substantially the same dimensions and configuration when it travels through passages 216 and 220, and eventually into the vertebral body. It will now be appreciated that when apparatus 20a and needle 120 are used together, the bone cement is carried through a substantially uniform path from tip 48a to tip 148.

Figure 7:
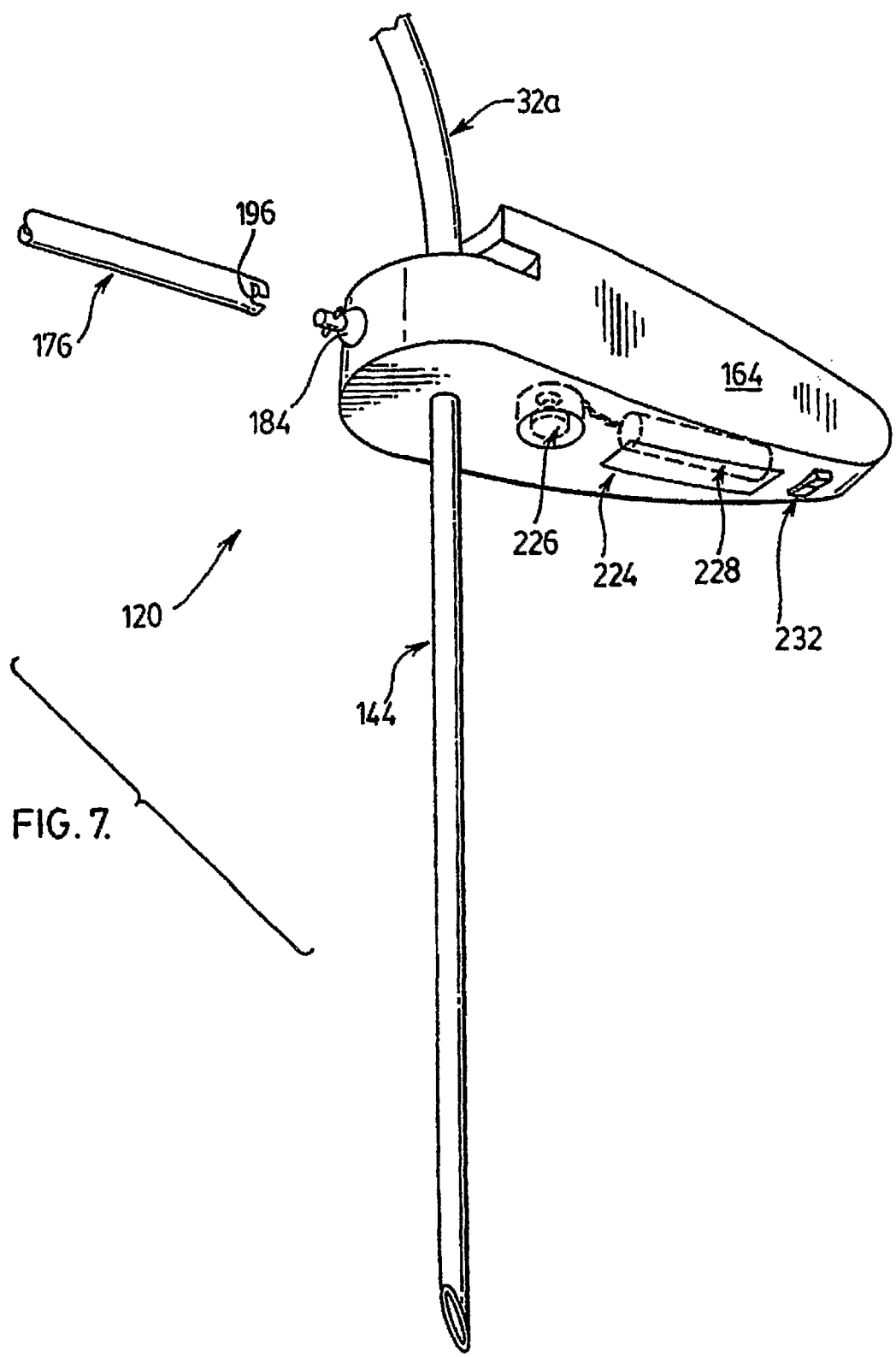
FIG. 7 shows a bottom isometric view of the needle of FIGS. 4-6.

Referring now to FIG. 7, needle holder 120 can also be provided with (though need not be) a vibrator 224. In a present embodiment, vibrator 224 includes an imbalanced micromotor 226, such as that commonly employed on a cellular telephone or wireless paging device. Micromotor 226 is housed within handle 152 and is sized in order to provide a vibrating force to duct 144 and thereby facilitate the flow of bone cement through passage 216 and 220, and thereby ease the infective force needed at plunger 44a. Micromotor 226 is powered by a battery 228 or other power supply housed within handle 152, and selectively turned on or off via a power switch 232 operably connected to both micromotor 226 and battery 228.

While only specific combinations of the various features and components of the present invention have been discussed herein, it will be apparent to those of skill in the art that desired subsets of the disclosed features and components and/or alternative combinations of these features and components can be utilized, as desired. For example, either apparatus 20 or apparatus 20a, or hybrids thereof, can be used with needle 120. Also, needle 120 need not include vibrator 224.

Additionally, while specific types of connections, fittings etc are shown for apparatus 20 and apparatus 20a and holder 120, (e.g. sets of complementary threads), a vast array of other fittings that will also achieve the result of a substantially uniform passage from a syringe (or other delivery reservoir) into a vertebral body (or other bone site) are within the scope of the invention. Indeed, a unitary construction along various points of the such a path can be employed in order to provide such a uniform path.

Still additionally, while polymethylmethacrylate has been mentioned as a common bone cement, other bone cements are within the scope of the invention. Such other bone cements include hydroxy apetite, calcium phosphate, calcium sulphate, calcium hydroxy apetite, or any other cement that may integrate with bone and form new bone. Because of the respective viscosities of these cements are higher than polymethylmethacrylate's, a non-luer lock system is provided. Further, the present invention allows for injection of any cement at lower pressures.]

The above-described embodiments of the invention are intended to be examples of the present invention and alterations and modifications may be effected thereto, by those of skill in the art, without departing from the scope of the invention which is defined solely by the claims appended hereto.

The invention claimed is:

1. A bone cement kit comprising:
   a needle comprising a trocar and a stylet;
   said trocar for injecting a bone cement into a bone and having a hollow duct extending between an open tip and a handle, said handle having an opening communicating with an interior of said hollow duct,
   said stylet receivable within said hollow duct to provide a solid instrument for piercing bone;
   a delivery reservoir for holding said bone cement, having a first distal tip with threads along a surface of said first distal tip;
   a connecting tube having a proximal end with threads along a surface of said proximal end, and a distal end opposite said proximal end with additional threads connecting to said trocar for injecting said bone cement into a bone;
   a connector joining said first distal tip to said connecting tube, said connector having a first end with threads complementary to said threads of said first distal tip, and a second end with threads complementary to said threads of said proximal end of said connecting tube;
   said handle opening having threads complementary to said additional threads of said connecting tube, for connecting said distal end of said connecting tube to said opening after removal of said stylet from said hollow duct;
   wherein said first distal tip, said connector, said connecting tube, said opening, said hollow duct and said open tip are configured with uniform internal dimensions so as to provide a uniformly dimensioned pathway for said bone cement to travel from said first distal tip through to said open tip.

2. The kit of claim 1 wherein said delivery reservoir is a syringe.

3. The kit of claim 1 wherein said bone is a vertebral body.

4. The kit of claim 1 wherein said bone cement is selected from the group consisting of polymethylmethacrylate, hydroxyapatite, calcium phosphate, calcium sulphate, calcium hydroxyapatite, or any other cement that may integrate with bone and form new bone.

5. The kit of claim 1 wherein said bone cement is PMMA and said delivery reservoir has a volume of about ten cubic centimeters and said uniformly dimensioned pathway has a diameter of between about five millimeters and about fifteen millimeters.

6. The kit of claim 1 wherein said bone cement is PMMA and said delivery reservoir has a volume of about ten cubic centimeters and said uniformly dimensioned pathway has a diameter of between about seven millimeters and about twelve millimeters.

7. The kit of claim 1 wherein said bone cement is PMMA and said delivery reservoir has a volume of about ten cubic centimeters and said uniformly dimensioned pathway has a diameter of between about eight millimeters and about ten millimeters.

8. The kit of claim 1 wherein said stylet comprises;
a shaft,
a piercing tip; and,
a grip located on the end of said shaft, opposite said piercing tip.

9. The kit of claim 8 wherein said piercing tip of said stylet is receivable into said opening of said handle.

10. The kit of claim 9 wherein said handle further includes a cut-away section, and a knob; said cut-away section complementary in shape to said grip of said stylet; and said grip and said cut-away section engageable for securing said stylet within said trocar.

11. The kit of claim 10 wherein said needle further having a lock for affixing said grip within said cut-away section.

12. The kit of claim 11 wherein said lock comprises a tab on said grip and a complementary groove on said handle; wherein said tab is engaged within said groove in the locked position, and disengaged from said groove in the unlocked position.

13. The kit of claim 1, said handle further having a vibrator for providing a vibrating force, wherein said vibrating force ilitates the flow of bone cement through said first passage and said second passage.

14. The kit of claim 13 wherein said vibrator comprises a micromotor; and a power supply for powering said micromotor.

15. The kit of claim 14 wherein said power supply is a battery.

* * * * *